United States Patent [19]

Behme

[11] Patent Number: 4,502,358
[45] Date of Patent: Mar. 5, 1985

[54] KNIFE HOLDER FOR SLIDING MICROTOMES

[75] Inventor: Werner Behme, Walldorf, Fed. Rep. of Germany

[73] Assignee: Parke, Davis & Company, Morris Plains, N.J.

[21] Appl. No.: 449,338

[22] Filed: Dec. 13, 1982

[30] Foreign Application Priority Data

Jun. 16, 1982 [DE] Fed. Rep. of Germany ... 8217317[U]

[51] Int. Cl.³ .............................................. B26D 1/02
[52] U.S. Cl. ...................................... 83/700; 83/856; 83/915.5; 144/155; 144/175
[58] Field of Search ........................ 83/915.5, 425, 662, 83/698, 699, 856, 707, 409, 709, 544–546; 30/293, 286; 409/134, 254; 144/155, 175, 184

[56] References Cited

U.S. PATENT DOCUMENTS

| 1,574,641 | 2/1926 | Christopherson | 30/286 |
|---|---|---|---|
| 1,765,283 | 6/1930 | Patterson | 83/915.5 X |
| 2,439,671 | 4/1948 | Ott | 83/915.5 |
| 2,662,445 | 12/1953 | Jacoby | 83/915.5 |
| 2,901,944 | 9/1959 | Sparer | 83/915.5 |
| 3,190,164 | 6/1965 | McCormick | 83/915.5 |
| 3,203,290 | 8/1965 | Ashby | 83/915.5 |
| 3,212,379 | 10/1965 | McCormick | 83/915.5 X |
| 3,220,290 | 11/1965 | Shandon | 83/915.5 |
| 3,227,020 | 1/1966 | Zeytoonian | 83/915.5 |
| 4,378,718 | 4/1983 | Kraft et al. | 83/915.5 X |

Primary Examiner—James M. Meister
Assistant Examiner—John L. Knoble
Attorney, Agent, or Firm—Alan H. Spencer; Stephen Raines

[57] ABSTRACT

A knife holder having two cylinders journaled for axial and rotatable movement are supported by two spaced-apart clamp blocks. The cylinders are axially and rotatably movable in the clamp blocks. Each cylinder has a continuous longitudinal slot of a cross-sectional shape generally complementary to the cross-sectional shape of the knife clamped therein. The axial movement of one cylinder relative to the other cylinder enables the length of knife edge that is exposed to be varied.

9 Claims, 4 Drawing Figures

KNIFE HOLDER FOR SLIDING MICROTOMES

BACKGROUND OF THE INVENTION

The invention pertains to a microtome knife holder for adjustably and firmly holding a microtome knife.

A microtome with a knife holder, for holding the cutting edge of a knife in a vertical position, whereby the knife can be adjusted on three axes which are perpendicular to each other, is described in German Auslegeschrift No. 21 43 529 published Aug. 30, 1971. The microtome has a carriage, i.e., the carrier for a specimen to be sectioned, which is moved vertically up and down. This structure is very practical for sectioning soft and small specimens because only minor cutting forces are required and it is necessary to only produce sections of limited length.

A microtome of the general structure referenced is provided with a cantilevered knife blade, i.e, the blade is supported by only one end, and is commonly utilized in the preparation of sections of frozen relatively soft body tissue.

However, when cutting hard and large specimens, such as for microscopic examination of metallurgical specimens or bony body tissue it is very important that the microtome be capable of enabling the use of cutting forces of a high magnitude and also that relatively long sections can be produced.

In addition prior art microtomes require mounting of knives of different lengths when sectioning specimens of different sizes, whereas the present invention enables the selective adjustment of the effective cutting or sectioning blade length.

SUMMARY OF THE INVENTION

The principal object of the present invention is to provide a knife holder for a microtome wherein large relatively hard specimens may readily be sectioned in preparation for microscopic examination.

The knife holder according to the present invention is constructed in such a manner that the knife blade is held, or supported, from both ends and wherein a relatively short length of the so supported blade is actually used, at any given time, for sectioning of the specimen.

In a preferred embodiment of the invention the opposite end portions of an elongated knife blade are clamped in jaw members axially and longitudinally adjustably journaled in spaced-apart support members carried by a base that is adapted to also support a specimen carriage adapted to reciprocate on a plane generally parallel to the surface of a specimen to be sectioned for microscopic examination. In a preferred embodiment the jaw members comprise generally cylindrical members having a knife receiving slot within which the end portions of the blade can be clamped.

Each end portion of the knife is held in a respective cylinder, leaving the middle portion of the knife, i.e., the cutting area or edge exposed. It will be understood that the extent of the exposed portion of the blade edge corresponds to the size of the specimen. The ability to adjust the extent of the knife is very important in microtomes with a horizontally movable specimen carriage which is very useful for large section lengths and, through which, large and precise specimen sections can be obtained. The stable lateral positioning of the cylindrical knife holders and their clamp blocks provides a reliable adjustable holding device for a knife clamped therebetween.

In use the specimen to be sectioned is mounted, or "blocked," on a carriage that moves towards the knife edge, the cutting angle of which has previously been adjusted. The clamp blocks are identical and hold the cylinders which are identical, but for the fact that they are generally "mirror images." The clamp blocks are movable perpendicular to the cutting movement. The length of the knife exposed, i.e., unsupported, can be adjusted by axial movement of these cylinders through the clamp blocks. In this way only a knife distance corresponding to the width of the specimen is not supported. Therefore, great sectioning forces can be effected in this manner, which forces are necessary for cutting hard objects such as in metallography.

According to the invention, the microtome provides a knife holder suitable for specimens of different sizes. The present invention ensures that the open space or unsupported portion of the blade corresponds to the size of the specimen which has to be sectioned. The clamp blocks are also vertically adjustable.

The cylinders in the clamp blocks are rotatable so that the cutting angle of a knife can be adjusted in a wide range. If required, the unsupported part of the knife can be supported by a reinforcement means, in order to avoid a bending of the knife. The cylinders are axially movable and rotatable and can also be fixed in selected positions. In each of these cylinders there is a continuous longitudinal slot in which an end portion the knife is inserted, and wherein the cross-sectional configuration of the slots generally corresponds to the cross-sectional shape of the knife. These slots are generally wedge-shaped in cross-section, with the point of the wedge facing forward toward the specimen carriage. The knife also can be moved forward in these slots, i.e. it can be moved in the direction toward the knife edge in order to be able to clamp resharpened knives having a modified (reduced) cross-section. The cylinders have circular cross-sections and the center of the circle corresponds to the axis of rotation of the holding device. The knife can be rotated around the axis, and in this way it can be adjusted to the required cutting angle.

The narrow portion of the slots in the cylinders, in which the knife is inserted, is provided with resilient longitudinally extending spacers positioned adjacent the wedge point portions of the slots. These prevent contact of the rather delicate knife cutting edge with the cylinder adjacent the wedge point of the slot and also function to prevent shavings or other debris from working its way into the wider parts of the slot between the knife and the wall of the cylinder defining the slot. The slot can be provided with adjusting means such as set screws for locking the knife blade in position.

Although the longitudinal axis of the knife is normally perpendicular to the cutting movement of the specimen carriage, which is generally movable on a horizontal plane, means providing for mounting of the clamp blocks parallel, but at an angle to the travel of the specimen carriage is also desirable in order to start cutting from one edge of the specimen. The knife, in such instance, is held between the two angled, opposing and parallel clamp blocks. The clamp legs are also parallel fastened on the microtome base or frame in the direction of the cutting movement of the carriage. Cutting from the edge of the specimen can also be accomplished with a very small distance between the clamp blocks whereby the position of the knife is not square but is located in a given angle to the direction of the movement of the carriage.

The exposed portion of the knife edge has a knife protector which comprises, in each cylinder, a bar mounted for axial sliding movement. The bars are independently movable in longitudinally extending grooves in the cylinders wherein they can be extended outwardly of each respective cylinder to "cover" or protect the exposed portion of the knife between the cylinders.

DETAILED DESCRIPTION OF THE INVENTION

Figure 1:
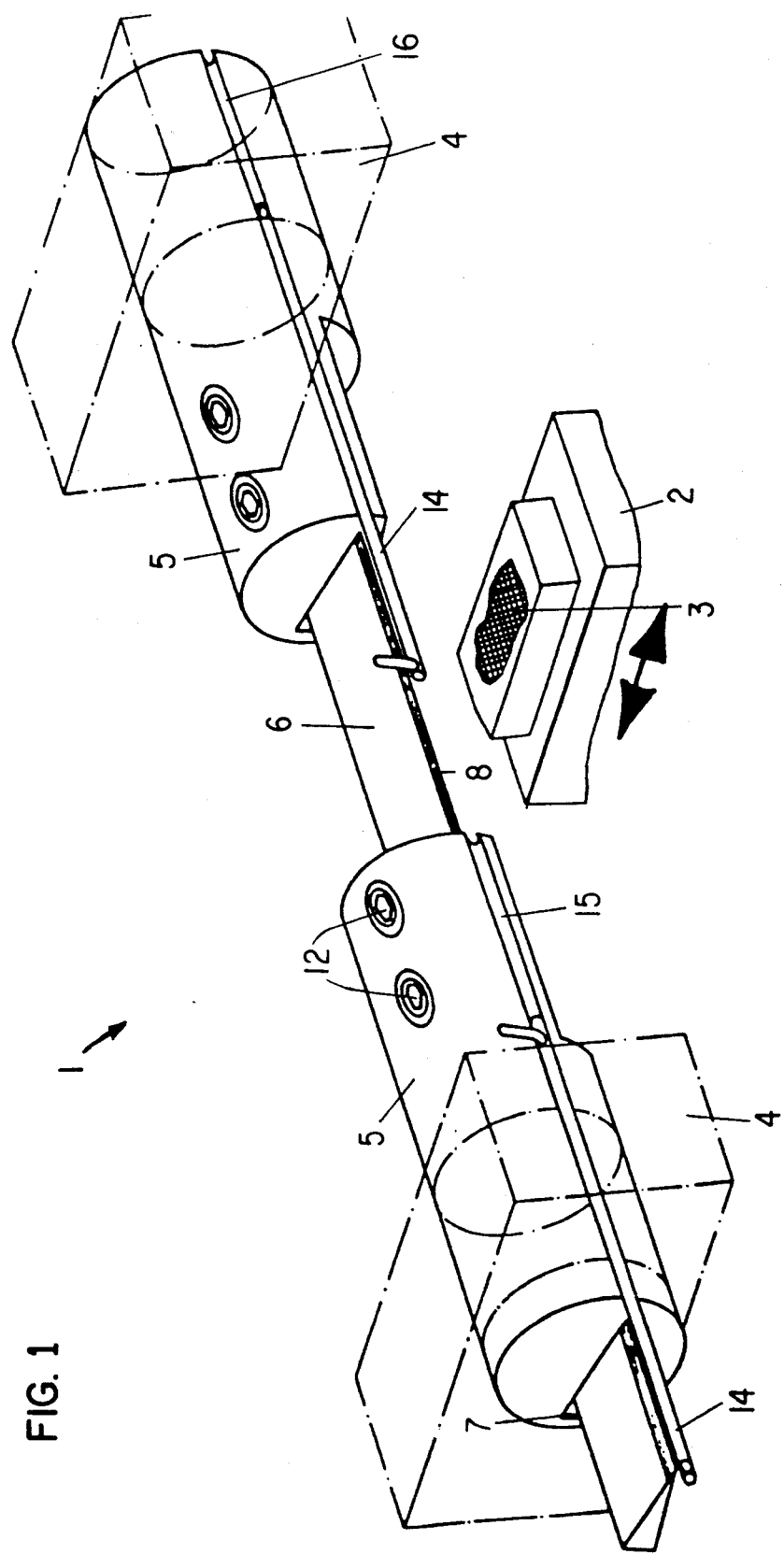
FIG. 1 is a schematic perspective of an embodiment of a horizontal knife holder in accordance with the invention with a knife mounted therein and wherein a specimen holding carriage is generally indicated with a specimen to be sectioned mounted thereon.

Turning now to FIG. 1 it will be seen that the knife holder device is indicated generally at 1 and is supported on a base, not shown, on both sides of a specimen carriage 2 which is movable on a horizontal plane. On the carriage 2 is mounted the specimen 3 that is to be sectioned. A knife 6, horizontally positioned, is held, or locked, in adjustable knife holder means or cylinders 5, obliquely to the direction of the movement, as shown by a double arrow, of the specimen carriage 2.

Figure 3:
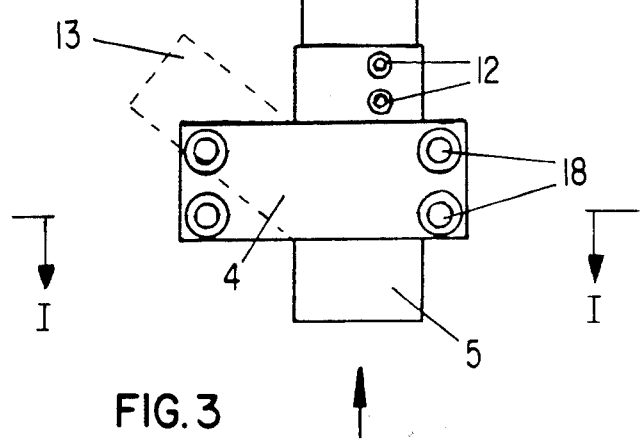
FIG. 3 is a schematic cross-section taken along the plane of the section line 3—3 of FIG. 2, with the knife having been removed.
Figure 3:
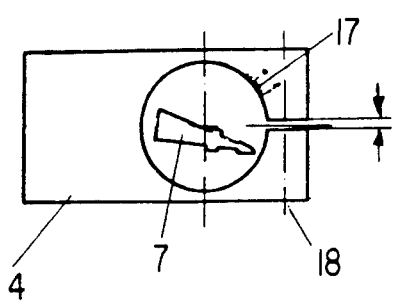
Figure 4:
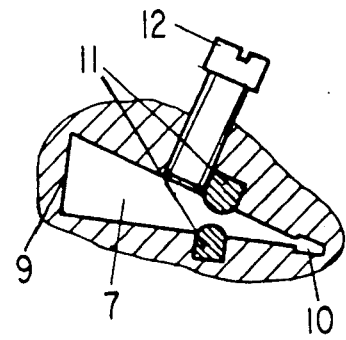
FIG. 4 is fragmentary enlarged cross-section of FIG. 3, with a portion shown in side elevation, to more clearly show the slot in the blade holder cylinder.

The two laterally disposed knife holder cylinders 5 are of a mirror image construction. Each cylinder 5 is adjustably supported in a clamp block 4 which is vertically adjustable and has a horizontally disposed cylindrical through bore, or hole 4'. The hole 4' receives a cylinder 5 comprising a knife holder or clamping means, which is selectively adjustable on an axis normal to the direction of the movement of the specimen carriage 2. The knife holder cylinder 5 has, as best seen in FIGS. 3 and 4, a wedge-shaped continuous through bore 7 generally corresponding to the cross-sectional shape of the knife 6. The bore 7 is normal to the direction of the carriage movement, i.e., extends longitudinally of the cylinder 5.

In the exemplary embodiment shown, the knife 6 is of a "wedge" cross-section and is held in the bore 7 of each of the cylinders 5 horizontally at a vertical height that enables sectioning contact of the knife 6 with the specimen 3 on the carriage. The described construction of the cylinders 5 holding the knife 6 allows a longitudinal adjustment of the knife, crosswise or normal, to the direction of the carriage 2 movement. The cylinders 5 can be adjusted so that the exposed portion of the knife edge 8 is variable so as to generally correspond to the specimen 3 width, i.e., the length to blade 6 exposed can be adapted to the specimen width. The ability to adjust the exposed portion of the blade is a significant aspect of the invention since it greatly reduces the danger of bending or twisting of the knife 6. This is especially so because the support of the knife can be adjusted in a way that only the extent of the knife edge necessary for sectioning the specimen is left open, i.e., unsupported.

For the protection of the knife edge 8 and for protection of a microtome operator bars 14, slidably received in grooves or guideways, 15, 16 are provided in the leading edge of the cylinders 5. These bars 14 are disposed in parallel relation to the cutting edge 8. The bars 14 are of sufficient length that the inside and/or outside extents of the cutting edge which are exposed, and are not used for cutting, ar protected as shown in FIG. 1.

Figure 2:
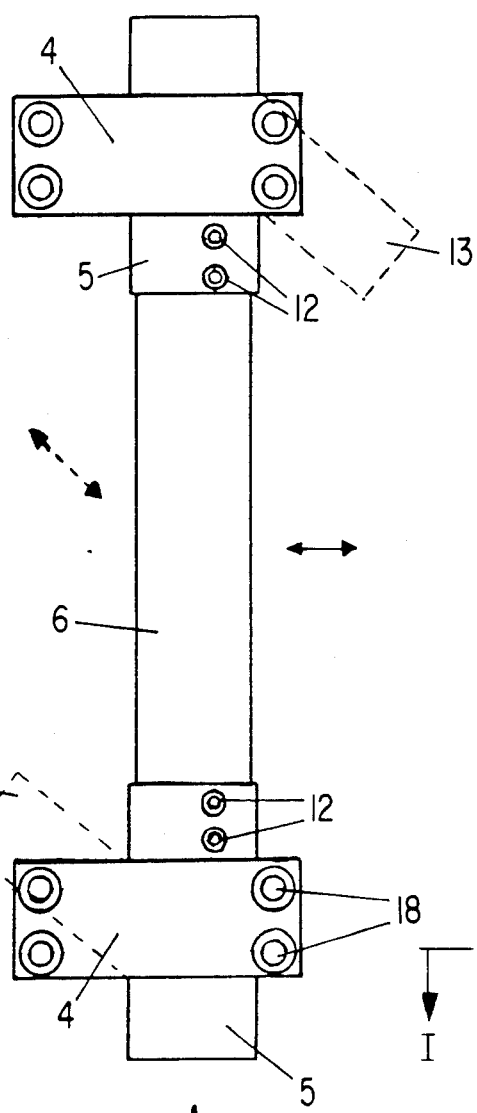
FIG. 2 is a schematic top view, in reduced scale of the knife holder of FIG. 1, the carriage not being shown, wherein there is shown in phantom lines an alternative construction.

In addition to providing means for adjusting the length of knife edge 8 exposed, the invention also provides means for adjustment of the height and the clearance angle of the knife 6 relative to the specimen 3 to be sectioned. The height adjustment is accomplished by selectively adjusting the height of the clamps 4 by covnentional means not shown. The cutting angle of the knife 6 is adjusted by rotating the cylinders 5 in the bores 4' of the clamps 4. The rotation angle of an adjustment can be read by providing a graduated scale 17 at one side of each of the clamps 4 as is shown in FIG. 3 in conjunction with one clamp 4. After the knife 6 has been adjusted in relation to the size of a specimen which is to be sectioned, the knife 6 ends are releasably fixed relative the cylinders 5 by means of radially extending clamping bolts 12 received in threaded bores that communicate with the bore 7. The cylinders 5 can be releasably locked in the clamp blocks 4 by clamping means comprising bolts 18 as best seen in FIGS. 2 and 3. Each clamp block 4 has a slot of the width "s," see FIG. 3 right side, which communicates with bore 4' so that the clamping bolts 18 can be tightened so that the diameter of the clamp bore 4' is reduced and, in this way, the cylinders 5 are firmly clamped so that the cylinders 5 are not rotatable or longitudinally movable.

In a preferred embodiment the through bores or slots 7 of the cylinders 5, adjacent the narrow portion, on both surfaces defining the wedge-shaped bore 7 are optionally provided with longitudinally extending resilient snubbers 11 as best seen in FIG. 4, which cooperate to position the knife 6 in the center of the slot 7 to keep the cutting edge from touching the point 10 of the slot as might dull or damage the knife. Means for adjusting the knife 6 within the cylinders 5 include the clamping bolts 12, see FIG. 4, which go through the cylinder 5 into the slot 7. In the area of the slot base, or wedge base 9, adjustable through bolts, now shown, similar to bolts 12 may be provided in order to decrease the effective rearward extent of the slot 7 so as to move a knife that has been narrowed due to frequent resharpening toward the slot point 10.

As will be seen in FIG. 2 in addition to enabling adjustment of the knife position vertically relative to the direction of movement of the carriage 2 the clamp block 4, can also be fixed at a diagonal relative to the direction of movement of the specimen carriage. This alterante positioning of the clamp blocks is illustrated in phantom lines. In this embodiment the clamp blocks 4 are assembled to the frame base of the microtome instrument, not shown, so that clamp blocks 13 are positioned parallel to each other and firmly mounted on the frame base, so the relative movement between the carriage 2, see the double broken line arrow in FIG. 2, and the knife 6 is at a diagonal. The purpose of the diagonal "positioning" of the knife 6 is to start the sectioning at the edge of a specimen, i.e., at a diagonal to the major axis of the specimen. This is necessary for the sectioning of certain specimens to avoid damage to the knife or alteration of the morphology of the specimen.

From the foregoing it will be appreciated that the microtome knife holder comprising the present invention may be adapted to cooperate with microtome devices of various basic structures generally merely by providing means for mounting the clamp blocks 4 or 13. It will also be appreciated that the relative movement between the knife and specimen may be accomplished by reciprocation of the knife holder as opposed to the specimen carriage.

I claim:

1. In a sliding microtome having a specimen holder, a knife, and two knife mounts, one of said mounts being positioned on one side of the specimen and the other of said mounts being positioned on the other side of said specimen, the improvement comprising two elongated knife holders, each holder having a longitudinally extending bore adapted to encase a portion of the knife and being longitudinally slidable in a respective mount, lock means for releasably clamping each holder in a respective mount to selectively position each holder whereby the amount of knife exposed between said holders may be varied.

2. The improvement of claim 1 wherein the holders have generally cylindrical portions journaled in the mounts for rotational and longitudinal adjustment.

3. The improvement of claim 2 wherein each longitudinally extending bore has a knife edge relief gap.

4. The improvement of claim 3 wherein each bore has a cross-sectional configuration generally complementary to the cross-sectional configuration of a knife to be held therein.

5. The improvement of claim 3 including means for adjustably positioning a knife laterally within each bore.

6. The improvement of claim 5 wherein said means for lateral adjustment of a knife comprises adjustable stop means for urging a knife toward the direction of cutting engagement.

7. The improvement of claim 3 wherein each through bore is provided with snubber means for positioning a cutting edge of a knife supported therein.

8. The improvement of claim 3 including guard means for temporarily protecting the exposed edge of a knife.

9. The improvement of claim 8 wherein each member has a longitudinally extending slot and said guard means includes two manually slidable rods each being slidably mounted in a respective slot.

* * * * *